(12) United States Patent
Heller et al.

(10) Patent No.: US 7,154,016 B2
(45) Date of Patent: Dec. 26, 2006

(54) ATOMIZED POLYSULFIDE USED IN ETHYLENE STEAM CRACKER

(75) Inventors: Fred E. Heller, Uniontown, OH (US); Charles D. Roberts, Willoughby Hills, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 269 days.

(21) Appl. No.: 10/475,457

(22) PCT Filed: Mar. 6, 2002

(86) PCT No.: PCT/US02/06918

§ 371 (c)(1),
(2), (4) Date: Oct. 3, 2003

(87) PCT Pub. No.: WO02/081595

PCT Pub. Date: Oct. 17, 2002

(65) Prior Publication Data

US 2004/0122277 A1    Jun. 24, 2004

Related U.S. Application Data

(60) Provisional application No. 60/282,030, filed on Apr. 6, 2001.

(51) Int. Cl.
*C07C 4/02*    (2006.01)
(52) U.S. Cl. .................. 585/652; 585/648; 585/950
(58) Field of Classification Search ................ 585/648, 585/652, 950
See application file for complete search history.

(56) References Cited

U.S. PATENT DOCUMENTS

| | | | | |
|---|---|---|---|---|
| 4,708,787 A | * | 11/1987 | Peters et al. | 208/130 |
| 5,120,892 A | | 6/1992 | Skraba | 585/652 |
| 5,264,114 A | | 11/1993 | Dunbar | 208/48 HA |
| 5,284,994 A | * | 2/1994 | Brown et al. | 585/648 |
| 5,435,904 A | | 7/1995 | Reed et al. | 208/48 AA |
| 5,625,111 A | * | 4/1997 | Astbury et al. | 585/653 |
| 5,777,188 A | | 7/1998 | Reed et al. | 585/648 |
| 5,944,961 A | * | 8/1999 | Gandman | 202/241 |
| 6,228,253 B1 | * | 5/2001 | Gandman | 208/48 AA |

FOREIGN PATENT DOCUMENTS

WO    WO 97/45506    12/1997

OTHER PUBLICATIONS

Search Report from corresponding PCT International Publication No. WO 02/081595 published Oct. 17, 2002.

* cited by examiner

*Primary Examiner*—Glenn Caldarola
*Assistant Examiner*—In Suk Bullock
(74) *Attorney, Agent, or Firm*—Samuel B. Laferty; Michael F. Esposito

(57) ABSTRACT

Dialkyl polysulfides can be added to hydrocarbon gas fed streams for alkene steam crackers for the petrochemical industry. The polysulfides act as sulfiding agents for surfaces of the steam crackers and thereby reduce coking and CO generation. A preferred polysulfide is a di-t-butyl polysulfide. Such compounds tend to have lower vapor pressure, reasonable viscosities, and are relatively nonflammable as compared to the lower molecular weight sulfur containing compounds.

13 Claims, No Drawings

ATOMIZED POLYSULFIDE USED IN ETHYLENE STEAM CRACKER

This application is a National Stage Application of International Application No. PCT/US02/06918, filed Mar. 6, 2002, which claims the benefit of Provisional Application No. 60/282,030, filed Apr. 6, 2001.

FIELD OF INVENTION

Small amounts of sulfur containing chemicals are used as additives in ethylene steam crackers to prevent coking and other undesired chemical reactions. The sulfur sources are typically characterized as, sulfiding agents. Low molecular weight sulfur containing agents present fire and toxicological hazards due to their volatility. The polysulfidic sulfur containing agents have lower volatility and lower flammability.

BACKGROUND OF THE INVENTION

The use of sulfur compounds in feed streams to ethylene steamcrackers (both thermal and catalytic) has been known for many years to reduce coking rates and to reduce CO (carbon monoxide) production in the pyrolysis section of steamcracker furnaces. Others characterize the contribution of the sulfur compounds with improved reaction speed and product selectivity along with delaying or decreasing the frequency of de-coking of the reactors (lengthening the time between de-coking procedures). The sulfur sources are called sulfiding agents and are believed to decompose to form sulfidic surfaces on the insides of the reactors.

Sources of sulfur compounds have included 1) naturally occurring sulfur in feed (i.e. use of sour feed), 2) inexpensive odiferous sulfur compounds, which are also used for hydrotreater catalyst sulfiding. In particular the natural sulfur in good feedstocks has worked well with Co/Mo catalysts. As poorer quality feedstocks were used the sulfur content had higher thermal stability and required extremely high temperatures to activate the catalyst. Also as more sophisticated catalysts were made with greater hydrogenating and cracking power, they benefited from higher degrees of sulfurization than was possible with the feedstock. The preferred inexpensive odiferous sulfur compounds include DMDS (dimethyl disulfide) or DMS (dimethyl sulfide).

DMDS has a flash point of 15° C., a boiling point of 110° C., a strong odor and is a powerful solvent for many polymers. DMS has a flash point of <−18° C. and a boiling point of 36–39° C. Both compounds have strong odors, require grounded equipment, and require operators in contact or potential contact with the chemicals to have goggles, gloves, and an air supplied respirator.

SUMMARY OF THE INVENTION

It has been discovered that low viscosity relatively non-volatile polysulfides can be used as sulfiding agents in gas fed alkene (ethylene) thermal steam crackers. Preferable embodiments are non-catalytic ethylene steam crackers which rely predominantly on thermal cracking, although embodiments using catalysts are not precluded. While the polysulfides, due to their molecular weight, typically can't be volatilized in the 20–40° C. hydrocarbon gas streams feeding the gas fed ethylene crackers, they can be dispersed as a fine spray using a spray nozzle or atomizer. These fine sprays can be carried into the heated portion of the reactor where they readily volatilized and thermally decomposed to sulfide the inner surfaces of the reactor. These reactors typically are not catalytic (using a catalyst) but are usually simple thermal crackers.

DETAILED DESCRIPTION OF THE INVENTION

The use of sulfur compounds in thermal and catalytic crackers is well known. The sulfur compounds are thermally decomposed and act as sulfiding agents. In the past there have been conflicting objectives with these sulfur compounds. It was desirable to use volatile sulfur compounds with low thermal decomposition temperatures such as dimethyl disulfide. While such compounds that were easily volatilized and thermally decomposed to achieve the objective, they also had low flash points, extremely objectionable odor, and toxicity (the toxicity was especially troublesome as these compounds have high vapor pressures).

Among the low molecular weight organic compounds with relatively high amounts of the active sulfur components one can identify dimethyldisulfide, dimethylsulfide, hydrogen sulfide, carbon disulfide, methylmercaptan, ethylmercaptan, and n-butylmercaptan. Dimethyldisulfide is preferred among these compounds for a variety of reasons, including its low thermal decomposition temperature, relative to the others, and the fact that it produces very little unsaturated hydrocarbon compounds on thermal decomposition. These unsaturated hydrocarbon compounds are thought to be significant contributors to coking in crackers, which is undesirable. All of these low molecular weight compounds have significant vapor pressure at 20° C. and flash points of 16° C. or less making them hazardous to ship and handle.

In recent years some ethylene producers have considered using lower odor polysulfides in liquid fed (naphtha or gas oil) ethylene steam crackers to minimize odor and decrease worker exposure to the volatile and more hazardous low molecular weight sulfur compounds. The polysulfides, such as t-nonyl polysulfide, were soluble in the liquids and could be conveniently added to the liquid feed prior to addition to the steam cracker. Since the polysulfides are liquids at 20–25° C. and have fairly low vapor pressure at those temperatures, there was no easy way to add polysulfides to gas feeds for ethylene crackers. The polysulfides, since they typically carry 2 to 8 sulfur atoms per molecule, have comparable sulfur content to dimethylsulfide (DMS contains 51% S, within the polysulfide range, while DMDS contains 68% S).

It has been discovered that some of the less viscous polysulfides, such as SulfrZol 54 di-t-butyl polysulfide, having a viscosity of 14 cps at 20° C. can be finely dispersed or atomized into the gas feed streams for an alkene steam cracker such as an ethylene steam cracker. Desirable polysulfides for this purpose have viscosities between 1 and 50 cps at 20° C. as measured by a Brookfield viscometer. This can be accomplished by inserting a metering system on the polysulfide to add the correct amount of polysulfide and a nozzle or atomizer, drawing from the polysulfide source and inserted in the hydrocarbon gas stream somewhere before the alkene steam cracker. Desirably the nozzle or atomizer is inserted a few inches or a few feet (about 1 to about 50 or 100 feet) before the manifold that immediately precedes the various reactor tubes of the alkene steam cracker. The proximity of the nozzle or atomizer to the manifold can minimize the time that the fine dispersion of polysulfide needs to stay suspended in the gas stream before the polysulfide enters the reactor tubes where it is almost simultaneously volatilized and decomposed. If the nozzle or atomizer is moved further upstream from the manifold the quality of the dispersion of polysulfide would advisably be increased to minimize the amount of polysulfide that is deposited on the walls of the pipe used to feed the manifold.

The polysulfides of interest would typically have the formula R—$S_x$—R where R is a linear or branched alkyl of 3 to 15 carbon atoms and x is either an integer between 3 and 8 or R—$S_x$—R is a blend of compounds where x varies between 1 and 8. In a typical SulfrZol 54 type of product x can be 4 for about 30–50 number percent of the molecules and values of 3 to 6 for about 80–95 number percent of the molecules. Trace amounts of molecules where x is 1, 2, 7, or 8 are present. Desirably R would be a linear or branched alkyl of 3 to 10 carbon atoms, and most preferably t-butyl. In a preferred embodiment at least 50% of the R groups are t-butyl groups.

The polysulfide may be formed into a dispersion by a variety of techniques. If the polysulfide is of sufficiently low viscosity it might simply be sprayed as a fine mist. A gas assisted spray nozzle or atomizer may be used to provide further shear to the liquid polysulfide to reduce the particle size. The gas of the gas assist might include relatively inert gases such as nitrogen or argon or hydrocarbon gases such as natural gas or propane. The hydrocarbon gas for gas assisted spray nozzles desirably has an average carbon length of 4 or less. The hydrocarbon gas feed stream typically operates from a few pounds pressure up to several hundred pounds pressure with a preferred range being from about 50 psig to about 150 psig. The hydrocarbon gas feed streams typically are fed at a temperature of less than 100° C. and more typically at ambient outside temperature (e.g. 10–40° C.). Multiple spray nozzles or atomizer tips may be used to increase the efficiency of forming the dispersion. A diluent may be added to the polysulfide to further reducing the viscosity of the polysulfide. A supercritical liquid may be added to the polysulfide to both reduce the viscosity and to volatilize from any droplets formed, further reducing their size.

It is anticipated that the dispersion of polysulfide in the gas stream would exist for about 1 to about 30 seconds, more preferably from about 5 to about 20 seconds before the polysulfide reached the warmer zones of the reactor tubes where it would be volatilized and thermally decomposed. The spray droplet sizes would be determined based upon this time and the calculated flow rate in the hydrocarbon gas stream to the alkene steam cracker.

The amount of polysulfidic compound added to the hydrocarbon feed to the alkene steam cracker would depend on the amount of sulfur already existing in the hydrocarbon feed and the sulfur requirements of the particular alkene steam cracker. More sulfur, in the form of a polysulfidic compound, may be added initially to a cracker after coke cleaning or other assembly or maintenance operations. In this embodiment typically at least 10 ppm or 50 ppm of sulfur is added in the form of a polysulfidic compound, based on the weight of the hydrocarbon gas stream. More desirably from about 20 to about 300 ppm of sulfur is added as the polysulfidic compound and preferably from about 50 to about 250 ppm of sulfur is added as the polysulfidic compound. Typically the amount of sulfur for continuous production is adjusted between about 50 and 400 ppm based on the weight of the hydrocarbon feed stream, and more desirably from about 75 to about 300 ppm. These amounts are adjusted based on the perceived rate of coking occurring in the reactor and the amount of CO (carbon monoxide) being generated by the process. Adding more sulfur to the hydrocarbon feed stream, if there is a deficiency of sulfur, typically reduces coking and the amount of CO produced. Coke and CO are less desirable byproducts of the alkene steam cracking process. Eventually the amount of coke built up on the inside of the reactor reduces both flow rates and reaction efficiency such that the reactor is shut down and the coke is removed by a variety of processes.

The thermal decomposition temperature for SulfrZol 54 is about 160° C. while the thermal decomposition temperature for dimethyldisulfide (DMDS) according to the same method is about 200° C. and that for dimethylsulfide (DMS) is about 250° C. so there is actually a desirable decrease in the thermal decomposition temperature using this particular polysulfide. The vapor pressure of SulfrZol 54 is only 0.015 psia while that of DMDS is 0.54 and that for DMS is 14.9 so there is a decrease in the worker exposure to airborne sulfur compounds. Further the flash point of SulfrZol 54 is 100° C. while the flash point of DMDS is 15° C. and the flash point of DMS is <−18° C. Therefore there is a significant decrease in the hazards of shipping and storing the sulfur source for the sulfiding reaction.

The term ethylene steam cracker is used herein to describe the more general alkene steam crackers. The primary alkenes generated from these types of crackers are well known and characterized. They include ethylene, propylene, isobutylene and possible some of the conjugated dienes such as butadiene or isoprene. The preferred embodiment for this application is an ethylene steam cracker, which would produce primarily ethylene but possibly some other reaction products such as propylene would be recovered. The gas feed for these types of reactors would comprise hydrocarbon feed streams such as alkanes of substantially the same number or possibly slightly higher number of carbon atoms as the desired product. Desirably the hydrocarbon gas feed stream has a number average carbon chain length of less than 10 and more desirably less than 6. Thus it would be desirable in an ethylene steam cracker to have a substantial amount of ethane in the feed stream. Similarly for a propane steam cracker the feed would include an amount of propane. These hydrocarbon feed streams would typically be separated from petrochemical sources such as natural gas, refinery streams, or byproduct streams from a manufacturing plant.

The hydrocarbon gas fed alkene steam crackers differ significantly from liquid hydrocarbon fed alkene steam crackers. A primary difference is that the polysulfidic compounds will dissolve in liquid hydrocarbons facilitating their addition. In the gas fed steam crackers the polysulfidic compounds need to be dispersed as droplets in the gas stream. Gases vary from liquids in their viscosity, solvent power, and density. Liquids typically have densities of greater than 0.6, 0.8 or 0.9 g/cc. Gases typically have densities below those such as less than 600 g/liter, less than 300 g/liter or less than 100 g/liter even under relatively high pressures.

The alkenes derived from steam cracking can be used to make polyolefin polymers or can be further reacted to make other chemicals including the various ethylenically unsaturated monomers. The chemistry of "ethylene" is better described in the Kirk-Othmer Encyclopedia of Chemical Technology, 3rd edition volume 9 under the heading "ethylene". Pages 400 through 431 of that book discusses various methods of manufacturing ethylene including hydrolysis of hydrocarbons in tubular reactors, design of pyrolysis heaters, typical once through pyrolysis yields for various feedstocks (showing the recoverable hydrocarbons from cracking various feedstocks), table 5, pyrolysis heater characteristics (showing the operating conditions for a 20,000–70,000 ton per year ethylene production heater unit), and recovery and purification.

The ethylene steam crackers can be studied used quartz reactor tubes partially enclosed in a furnace to achieve the desired operating temperatures. Articles exist in the published literature where individuals study a variety of reaction condition changes, including the incorporation of various sulfur compounds on process performance. Such an article was title Simultaneous Thermal Cracking and Oxidation of Propane to Propylene and Ethylene by Choudhary, V. R.; Rane, V. H.; and Rajput, A. M. in AIChE Journal volume 44, no. 10 (1998-10) pp. 2293–2301.

Generally in tubular steam crackers the reaction temperatures are from about 750 or 800 to about 900° C. and the residence times are from about 0.1 to about 0.6 seconds. The reactor walls can be at higher temperatures to achieve this reaction temperature. Low hydrocarbon partial pressures are used. Steam is added to the feedstock to reduce the hydrocarbon partial pressure and the amount of carbon being deposited on the tube walls. The steam-to-hydrocarbon weight ratios usually vary from 0.3 for ethane to as high as 1.0 for gas oil feeds.

While the invention has been explained in relation to its preferred embodiments, it is to be understood that various modifications thereof will become apparent to those skilled in the art upon reading the specification. Therefore, it is to be understood that the invention disclosed herein is intended to cover such modifications that fall within the scope of the appended claims.

What is claimed is:

1. In a process for converting a hydrocarbon gas steam to an alkene using a steam cracker including providing a hydrocarbon gas stream, heating the gas stream to at least 750° C. to thermally crack the hydrocarbon gas stream, and recovering the alkene reaction product wherein the improvement comprises adding at least 10 ppm of an organic polysulfide having the formula R—$S_x$—R where R is a linear or branched alkyl of 3 to 15 carbon atoms and x is either an integer between 3 and 8 or R—$S_x$—R is a blend of compounds where x varies between 1 and 8 in the form of dispersed droplets to said hydrocarbon gas stream at a hydrocarbon gas stream temperature of less than 100° C. before said steam cracker based on the weight of said hydrocarbon gas stream.

2. In a process according to claim 1, where said organic polysulfide has a viscosity from about 1 to about 50 cps at 20° C. measured with a Brooktfield viscometer.

3. In a process according to claim 1, wherein R varies between 3 and 10 carbon atoms.

4. In a process according to claim 1, wherein R is a t-butyl group.

5. In a process according to claim 1, wherein said polysulfide is added using an atomizer with a gas assist.

6. In a process according to claim 5, wherein the gas assist is an inert gas such as nitrogen or argon or a hydrocarbon gas stream having a number average carbon chain length of less than 4.

7. In a process for increasing the sulfur content of a hydrocarbon gas stream including the steps of measuring the flow of the hydrocarbon gas and adding a sulfur containing organic molecule, at a temperature of less than 100° C., wherein the improvement comprises adding a sulfur containing organic molecule having the formula R—$S_x$—R where R is a linear or branched alkyl of 3 to 15 carbon atoms and x is either an integer between 3 and 8 or R—$S_x$—R is a blend of compounds where x varies between 1 and 8 as a fine dispersion of liquid polysulfide compound at a temperature below the thermal decomposition temperature of said liquid polysulfide compound.

8. A process according claim 7, wherein said hydrocarbon gas stream has a number average carbon chain length of less than 10.

9. A process according to claim to 8, wherein said hydrocarbon gas stream has a number average carbon chain length of less than 6.

10. A process according to claim 7, wherein R varies between 3 and 10.

11. A process according to claim 10, wherein R comprises at least 50% t-butyl groups.

12. A process according to claim 7, wherein said liquid polysulfide compound is added as an aerosol dispersion using a gas assisted spray nozzle.

13. A process according to claim 7, wherein said liquid polysulfide compound is added in an amount of at least 10 ppm based on the weight of said hydrocarbon gas.

* * * * *